United States Patent [19]

Janoski et al.

[11] 4,086,286

[45] Apr. 25, 1978

[54] ISOMERIZATION OF TETRAHYDROPOLYCYCLOPENTADIENES TO A MISSILE FUEL ADDITIVE

[75] Inventors: Edward J. Janoski, Havertown; Abraham Schneider, Overbrook Hills; Richard E. Ware, Aston, all of Pa.

[73] Assignee: Suntech, Inc., Wayne, Pa.

[21] Appl. No.: 720,306

[22] Filed: Sep. 3, 1976

[51] Int. Cl.$^2$ ................................................ C07C 1/00
[52] U.S. Cl. ............................... 260/666 PY; 60/208
[58] Field of Search .................. 260/666 PY; 60/208, 60/211; 149/109.6, 109.4

[56] References Cited

U.S. PATENT DOCUMENTS 3,864,178   2/1975   Rudy et al. ................... 149/109.6 X Primary Examiner—Stephen J. Lechert, Jr.
Attorney, Agent, or Firm—J. Edward Hess; Donald R. Johnson; Anthony Potts, Jr.

[57] ABSTRACT

Mixed tetrahydropolycyclopentadienes are isomerized in the presence of anhydrous aluminum trichloride to form an additive suitable for use with a high energy missile fuel. The amount of aluminum trichloride present is such that the weight ratio of trichloride to the tetrahydropolydiene is in the range between from about 0.005 to about 0.75. Also the isomerization involves an inert solvent and is at a temperature between from about $-20°$ C to about 25° C. Also anhydrous hydrogen chloride is present to facilitate the isomerization.

7 Claims, No Drawings

ISOMERIZATION OF TETRAHYDROPOLYCYCLOPENTADIENES TO A MISSILE FUEL ADDITIVE

BACKGROUND OF THE INVENTION

The invention herein described was made in the course of or under a contract thereunder with the United States Air Force Systems Command.

CROSS REFERENCE TO RELATED APPLICATIONS

This application is related to the following applications filed same date:

| Ser. No. | Inventors | |
|---|---|---|
| 720,308 | Richard E. Ware, et al | Isomerization of Tetrahydrotricyclopentadiene to a Missile Fuel |
| 720,305 | Abraham Schneider, et al | Process for Improving Low Temperature Properties of Tetrahydroalkyldicyclopentadiene |
| 720,307 | Abraham Schneider, et al | Isomerization of Endo-tetrahydrodicyclopentadiene to a Missile Fuel Diluent |

This invention relates to the preparation of an isomeric mixture of tetrahydropolycyclopentadienes. Hereinafter tetrahydropolycyclopentadienes are referred to as THPCPD. More particularly the invention relates to the preparation of an isomeric mixture from THPCPD. Still more particularly the invention relates to the catalytic isomerization of THPCPD containing at least two of the following: endo-tetrahydrodicyclopentadiene (endo-THDCPD), tetrahydrotricyclopentadiene (THTCPD), tetrahydrotetracyclopentadiene (THTeCPD), and tetrahydropentacyclopentadiene (THPeCPD).

The resulting isomeric liquid mixture can be used as an additive to high energy and/or high density missile fuel to increase the resulting heat of combustion (volumetric) and resulting density without adversely effecting the other properties. Also the resulting isomeric mixture can be used as a high energy and/or high density fuel by itself. High energy and/or high density missile fuel can be used in either jet or rocket propulsion. Jet propulsion includes a jet engine which can be used for a missile, aircraft and others and includes the three basic types, i.e., ramjet, turbo-jet and pulse jet. The term rocket generally refers to a device containing its own oxygen or oxidizing agent. An article in Aviation Week and Space Technology, Jan. 26, 1976, pages 111–113, discloses some of the high density hydrocarbon fuels that are under consideration as missile fuels, and to which the additive disclosed herein can be incorporated therewith.

U.S. Pat. No. 3,381,046 discloses the treatment of endo-tetrahydrodicyclopentadiene with an acidic reagent to effect isomerization to the corresponding exo-isomer. This patent also discloses generally that a Lewis acid, such as aluminum chloride, can be used to isomerize endo-tetrahydrodicyclopentadiene to its exo-form. However, it cautions that the isomerization can proceed beyond the exo-diene to form trans-decalin and admantane.

SUMMARY OF THE INVENTION

A mixture of THPCPD is isomerized using aluminum trichloride ($AlCl_3$) admixed with an inert liquid solvent and anhydrous hydrogen chloride. The isomerization occurs at a temperature and for a reaction time such that no measurable amount of undesired decalin and/or adamantane is formed. Further, the isomerization is such that the resulting isomerized mixture has properties enabling it to be used either as an additive to a high energy and/or high density missile fuel to increase its heat of combustion (volummetric) and its density or as a missile fuel by itself.

DESCRIPTION

Structures of the various THPCPD, along with their melting points, are as follows:

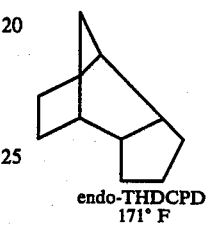

endo-THDCPD
171° F

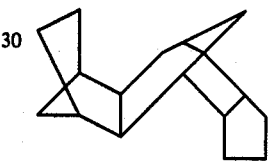

THTCPD
120° F

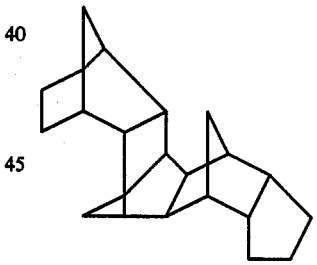

THTeCPD
355° F

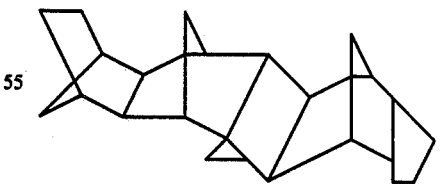

THPeCPD
very high melting

In the example of THDCPD the endo is used to designate the product in which the cyclopentane ring is turned in toward the cyclohexane ring. The other compounds whose structures are shown also have similar isomers.

Isomerization of the endo-diene results in the changing of the endo configuration to an exo configuration.

Thus an example of the resulting exo-THDCPD would have the following structure:

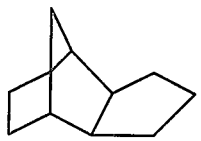

Further the isomerization, for example, of an endo-exo-endo THTCPD can result in an endo-exo-exo THTCPD which could be further isomerized to an exo-exo THTCPD, and subsequently as exo-exo-exo THTCPD. Thus four possible structures are as follows:

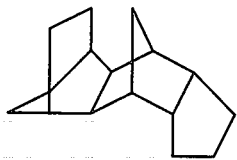

endo-exo-endo

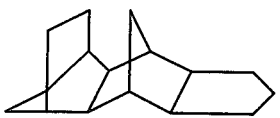

endo-exo-exo

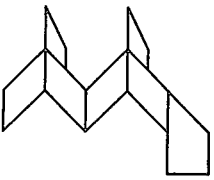

exo-exo-endo

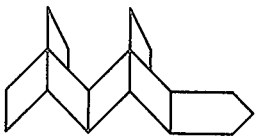

exo-exo-exo

The feed to the process of this invention is a THPCPD mixture which consists of at least two of the following: endo-THDCPD, THTCPD, THTeCPD and THPeCPD. While the feed can contain other similar hydrocarbons, such hydrocarbons should not adversely effect the isomerization or the catalyst. Further the similar hydrocarbons should not adversely influence the desired resulting properties of the isomerized mixture. Thus, for optimum results the feed consists essentially of THPCPD which itself can be a mixture of isomers.

Surprisingly, the isomerization of THPCPD can be controlled such that undesirable products such as decalin and adamantane can be avoided. Further surprising is that the controlled isomerization results in a product having a viscosity, a heat of combustion and a density making the product suitable for use in connection with a missile fuel.

The weight ratio of $AlCl_3$ to THPCPD is such that the isomerization can be controlled, otherwise undesirable compounds are made. Thus the weight ratio of $AlCl_3$ to the THPCPD is in the range between from about 0.005 to about 0.75, a preferable range is between from about 0.05 to about 0.25.

Anhydrous $AlCl_3$ is used. Any material which could adversely affect its effectiveness during the isomerization should not be present. For example, the presence of hydroxylic compounds such as water, alcohol or oxygen from air could deactivate the $AlCl_3$.

Anhydrous HCl is used to accelerate the reaction and enhance its activity. Such an effect is economically desirable. The HCl can be added to the process by various means, for example, by passing HCl gas through a liquid mixture of THTCPD and an inert solvent. All or some of the gas will dissolve in the mixture. The amount of HCl gas present can vary substantially; it can be in far excess of that necessary to saturate the liquid mixture or it could be substantially less than that necessary to saturate the mixture. However, the amount present should be effective to accelerate the reaction. A more operative range of HCl present is between from about 1000% to about 5% of an amount necessary to saturate the liquid mixture. A preferable range is between from about 200% to about 10% of that necessary to saturate the mixture.

An inert solvent is used. Since the reaction is mildly exothermic the liquid can serve as a heat sink. The liquid can also facilitate the handling of the contacting mixture and the resulting product. The liquid should not adversely react with the feed, product, or $AlCl_3$. Suitable inert solvents include chlorinated paraffins such as methylene dichloride ($CH_2Cl_2$), tetrachloroethane, pentachloroethane and other similar materials. Lower boiling solvents are preferred. Also the inert solvent series as a dissolving medium for the hydrogen chloride. As to the amount of inert solvent used, excessive amount can decrease the reaction rate and thus adversely effect the economics of a commercial operation. However, typically the weight ratio of the amount of solvent to the amount of THPCPD is in the range between from about 0.3 to about 1.5.

The isomerization temperature needs to be controlled between a narrow range. The lower limit can be influenced by the freezing point of the solvent and/or the rate of the reaction. While the reaction can proceed at a very low temperature the rate could be so slow as to be commercially unattractive. Thus generally the lower temperature limit is about $-20°$ C with about $-10°$ preferred. The upper limit is controlled by the formation of undesirable products which adversely effect properties of the resulting missile fuel. Also if the reaction rate is too rapid at an elevated temperature an uncontrolled exotherm could result. Thus generally the upper temperature limit is about 25° C with about 20° C preferred.

The pressure can vary substantially, however, economic consideration will favor a more limited range. Typically, the contacting will occur at atmospheric pressure. However, if a temperature is used which is greater than the boiling point of any solvent present then it might be advantageous to use a higher pressure to prevent the solvent from boiling away.

The properties of the resulting isomerized mixture can vary depending upon the element of isomerization that occurs. They can depend, in addition to the composition of the initial mixture, on how much of each of the particular THPCPD is present. Typically the resulting isomerized mixture will have a density (20°/4) in the range between from about 0.9075 to about 1.05 with a range between from about 1.02 to about 1.05 preferred. As to viscosity, the mixture would have a kinematic viscosity at 100° F in the range between from about 3 cst to about 25 l cst with a preferred range between from about 3 cst to about 20 cst. Since pour point is also a property to be considered for a missile fuel the resulting mixture can have a pour point of less than $-20°$ F and preferable it would be less than $-40°$ F. The net heat of combustion would be in the range between about 141,000 BTU/gallon to about 165,000 BTU/gallon with from about 154,000 BTU/gallon to about 165,000 BTU/gallon preferred.

To obtain an isomerized mixture having a density, a pour point and a viscosity which make it useful as an additive for a high density fuel for an air-breathing missile, the reaction time or contacting time should be sufficient to obtain the desired properties. Sufficient time depends in part on the amount of the tetrahydropolydiene isomerized, the amount of stirring; the amount of AlCl and HCl used, the configuration of the vessel containing the reaction or contacting mixture, and other variables. The amount of isomerization can be monitored during the process by measuring, for example, the viscosity thus when the desired amount of isomerization has been obtained, the reaction can be stopped.

The reaction can be stopped by removing the solvent. If the solvent has a relatively low boiling point it can be easily boiled off. After the solvent is removed the $AlCl_3$ and hydrocarbon tar, if any, can be easily separated, for example, by decantation. The tar and $AlCl_3$ together are often referred to as sludge. The amount of unreacted feed can be such that it can remain in the product without adversely effecting it. Then a washing with aqueous caustic of the isomeric mixture removes any remaining $AlCl_3$. Other means can be used to recover the isomeric mixture from the solvent and sludge. However leading the sludge in place in a reactor after removing the hydrocarbon phase, the sludge, fortified if necessary with an additional small quantity of fresh $AlCl_3$, can be used for isomerization of subsequent amounts of THPCPD.

The following examples illustrate embodiments of the present invention.

EXAMPLES

A mixture tetrahydropolycyclopentadiene was analyzed by vapor phase chromotography (VPC). The mixture consisted of the following hydrocarbons:

| | |
|---|---|
| endo-THDCPD | 32.5 wt. % |
| THTCPD | 47.6 wt. % |
| THTeCPD | 16.2 wt. % |
| THPeCPD | 3.7 wt. % |
| total | 100.0 wt. % |

The isomerization of the THPCPD mixture was performed in the following manner. Some (325 grams) of the filtered THPCPD mixture was charged to a suitable flask along with 424 gram of $CH_2Cl_2$, a solvent. The resulting combination was cooled to 0° C and then 51.6 grams of anhydrous solid $AlCl_3$ were added. Cooling to 0° C minimized any possible ring opening. After the $AlCl_3$ was added, the entire suspension was warmed to room temperature and then saturated at one atmosphere with anhydrous HCl. During the latter step the suspension acquired a light brown color. The flask containing the brown suspension was placed in a water bath maintained at 15°–18° C and the suspension agitated for five hours. The mixture was then frozen and stored overnight. The following morning it was heated to 10°–15° C and agitated for another 6 hours. At the end of 6.5 hours, after decantation of the liquid from excess $AlCl_3$, the flask was heated to 70°–80° C for about 10–15 mintues to boil off the solvent. After boiling off the solvent two layers remained. The lower layer contained about 107.9 grams. The separated, almost colorless, hydrocarbon layer was water washed and neutralized with caustic and after the latter was clear like water.

Then the treated hydrocarbon layer was distilled under vacuum. The tricyclic fraction boiled at 117°–139° C at 3 mm Hg. and about 115 grams was obtained. The latter had a density (20°/4) of 1.0265 and kinematic viscosity of 15.01 cst at 100° F.

Similar results are obtained when concentrations of $AlCl_3$, other than those shown, are used. Equally similar results are obtained when different amounts of solvents are used as well as when other solvents are used. Different amounts of the HCl also yield analogous results.

The invention claimed is:

1. Process for the isomerization of tetrahydropolycyclopentadiene comprising:
    (a) contacting a tetrahydropolycyclopentadiene mixture consisting of at least two of the following: endotetrahydrodicyclopentadiene, tetrahydrotricyclopentadiene, tetrahydrotetracyclopentadiene, and tetrahydropentacyclopentadiene; with anhydrous aluminum trichloride wherein the weight ratio of the amount of the aluminum trichloride to the tetrahydropolycyclopentadiene mixture ranges between from about 0.005 to about 0.75, and with anhydrous hydrogen chloride in an amount effective to accelerate the reaction and in the presence of a inert chlorinated paraffin solvent at a temperature in the range between from about $-20°$ C to about 25° C;
    (b) continuing the contacting unit isomerization of the mixture is sufficient to form a high density missile fuel or a high density missile fuel additive; and
    (c) recovering the resulting high density missile fuel or a high density missile fuel additive.

2. Method according to claim 1 wherein the inert chlorinated paraffin solvent is selected from the group consisting of methylene dichloride, tetrachloroethane and pentachloroethane.

3. Method according to claim 2 wherein the amount of the hydrogen chloride is in the range between from about 5 weight % to about 100 weight % of that necessary to saturate the contacting mixture.

4. Method according to claim 3 wherein the weight ratio of the amount of solvent to the amount of tetrahydropolycyclopentadiene mixture is in the range between from about 0.3 to about 1.5.

5. Method according to claim 1 wherein the missile fuel or the additive has a density (20°/4) in the range between from about 0.9075 to about 1.05 and a kinematic viscosity at 100%F in the range between from about 3 cst to about 25 cst and a pour point of less than $-20°$ F.

6. Method according to claim 5 wherein the weight ratio of aluminum trichloride to the mixture is in the range between from about 0.05 to about 0.25 and the temperature is in the range between from about −10° C to about 20° C and the amount of the hydrogen chloride is in the range between from about 10 weight % to about 200% required to saturate the system.

7. Process according to claim 1 wherein sludge, from a previous isomerization of the tetrahydropolycyclopentadiene, fortified with a small quantity of fresh aluminum trichloride, is used to contact and isomerize a subsequent amount of tetrahydropolycyclopentadiene.

* * * * *